United States Patent [19]

Dalla Bona

[11] 4,293,303
[45] Oct. 6, 1981

[54] JOINT FOR CONNECTING A PARTIAL DENTAL PROSTHESIS TO THE REMAINING NATURAL HUMAN TEETH

[76] Inventor: Hans Dalla Bona, Rousseauweg 9, 2563 Ipsach, Switzerland

[21] Appl. No.: 145,193

[22] Filed: Apr. 29, 1980

[30] Foreign Application Priority Data

Jun. 12, 1979 [CH] Switzerland .......................... 5466/79

[51] Int. Cl.³ ............................................ A61C 13/22
[52] U.S. Cl. .................................................. 433/177
[58] Field of Search ........................ 433/177, 170, 169

[56] References Cited

U.S. PATENT DOCUMENTS

| | | | |
|---|---|---|---|
| 2,660,789 | 1/1953 | Roccato | 433/177 |
| 3,372,483 | 3/1968 | Dalla Bona | 433/177 |

Primary Examiner—Robert Peshock
Attorney, Agent, or Firm—Wender, Murase & White

[57] ABSTRACT

A joint for connecting a partial dental prosthesis to remaining natural teeth has a compression spring (10) acting on joint portions (1, 7) displaceable in a sagital direction, which spring relieves the prosthesis (13) connected to one of the joint portions (7) in the unstressed state. The displacement of the joint portions when the prosthesis is stressed is delimited by the stop surfaces (14, 15) in such a manner that the spring (10) cannot be completely compressed. This protects the spring and its functional capacity is permanently ensured and an optimal distribution of the biting and chewing pressure acting on the prosthesis over the anchor tooth (3) and the gums (6) is also attained.

6 Claims, 2 Drawing Figures

JOINT FOR CONNECTING A PARTIAL DENTAL PROSTHESIS TO THE REMAINING NATURAL HUMAN TEETH

BACKGROUND OF INVENTION

The present invention relates to a joint for connecting a partial dental prosthesis to the remaining natural human teeth, whereby joint members connected to an anchor tooth or the partial dental prosthesis are telescoped without clearance and able to carry out relative movements extending only in one plane and whereby a spring acts between the two joint parts in order with the unstressed partial prosthesis to relieve its support.

DESCRIPTION OF THE PRIOR ART

A joint of this kind is described in the U.S. Pat. No. 3,372,483 and has various advantages described therein. The joint is mobile in one plane only and the spring may be made relatively strong although in practice the spring is often too weak to cause a desirable distribution of the chewing pressure acting on the prosthesis to the gums located beneath the prosthesis and to the anchor tooth. With increased stressing of the prosthesis, the spring becomes completely compressed and this has an adverse effect on the life thereof. If the spring force is considerably reduced by permanent deformation, or if the spring is broken, the prosthesis sinks in uncontrolled manner and the important relieving of the gums below the prothesis is no longer obtained.

SUMMARY OF THE INVENTION

It is an object of the present invention to improve the life and functional quality of the joint. This object is attained in accordance with the invention in that a stop is provided which limits the relative movement of the joint portions in the direction of the spring force. It is now possible for the limitation to be so effected that the stop action occurs before the spring has been completely compressed. This protects the spring which thus retains its full resilience for a longer time so as to lift the prosthesis off the gums, and, moreover, after stopping a substantially rigid transfer of the biting and chewing pressure onto the anchor tooth and the gums is obtained and cuts out excessive stressing of the spring. Nevertheless, should the spring eventually break, the stop prevents excessive sinking-in of the prosthesis whilst awaiting repair of the damage.

BRIEF DESCRIPTION OF THE DRAWINGS

The invention will be described further, by way of example, with reference to the accompanying drawings.

DESCRIPTION OF THE PREFERRED EMBODIMENTS

Figure 1:
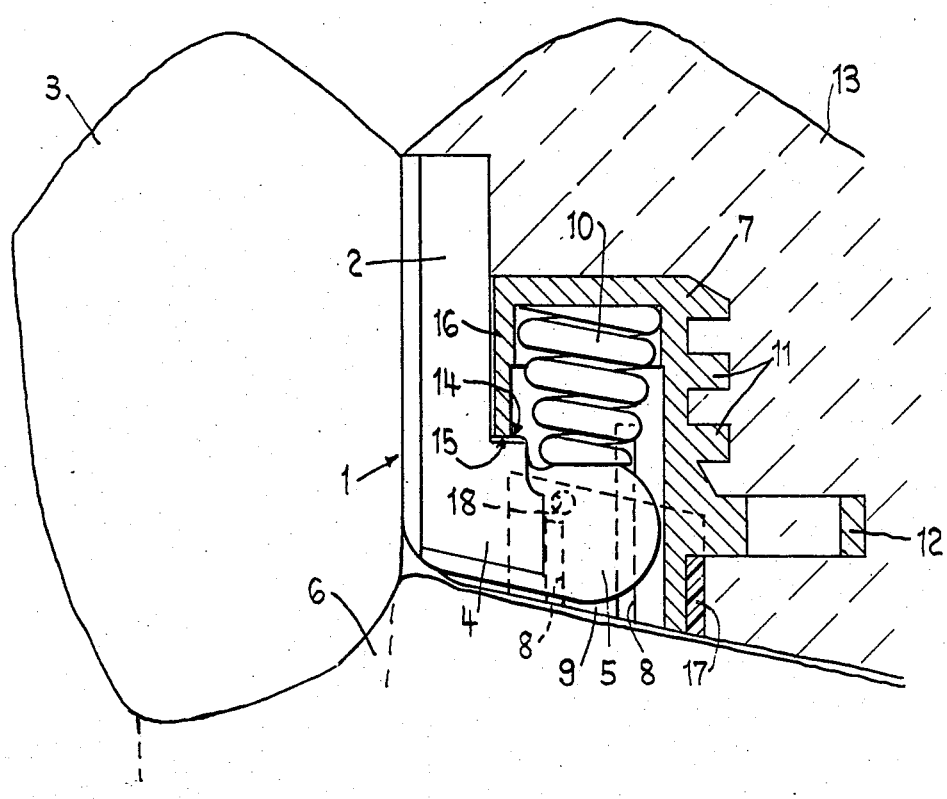
FIG. 1 shows the joint partly in section in the fitted, stressed state.
Figure 2:
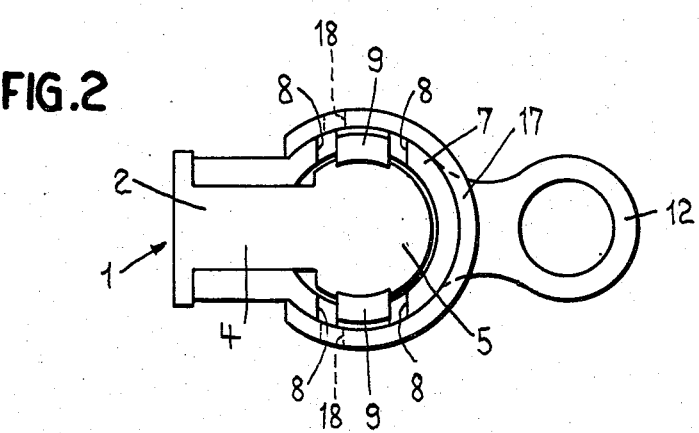
FIG. 2 is a plan view from below of the joint.

The joint has a first joint portion 1 having a rail 2 of T-shaped cross-section, which in the fitted state according to FIG. 1 is soldered to a crown or suitable filling of an anchor tooth 3. The joint portion 1 has a laterally projecting neck 4 at the normally lower end and the free end of the neck 4 is adapted as a ball joint or spherical coupling head 5. The lower outer surface of the neck is convexly radiused corresponding to the head 5 and merges tangentially into the head so that no shoulders or edges are formed. The lower end of the coupling member 1, when the prosthesis is relieved, may protrude slightly and abut against the gums 6, and hence does not cause any injury or irritation of the gums. Dental silk may be passed through at this point without being damaged or tearing.

The other coupling member is adapted as a sleeve 7 which is closed at the normally top end and open at the bottom end. At the lower open end the sleeve is provided with slightly inwardly bent resilient lugs 9 formed by slots 8 and which are so dimensioned that the spherical head 5 of the coupling member may be inserted into the sleeve 7 from below whilst slightly deforming the lugs 9 and then be retained therein. A compression spring 10 is located in the sleeve 7 and retains the unstressed prosthesis in an upper resting position determined by the abutment against the lugs 9 on the head 5. The sleeve is provided with ribs or lugs 11 and a ring 12 to improve its retention in the prosthesis material 13.

The neck 4 passes with parallel lateral surfaces through a lateral slot of the sleeve 7, which produces a mutual guidance of the joint portions in such a manner that they are able to move mutually in a sagital plane. A shoulder 14 is formed at the top end of the neck 4 and together with the underside 15 of the front wall 16 of the sleeve located above the slot, forms a stop.

A soft plastics material sleeve or gaiter 17, which has a cut-out in the region of the shoulder of the ring 12 is oriented when being mounted on this shoulder and engages around the lower end of the sleeve 7. The gaiter 17 is connected to the sleeve 7 by means of an adhesive compatible with use in the mouth, i.e. resistant to influences thereof (mouthproof). On installation it is cast into the prosthesis material 13 and the end is provided with at least one hole 18 into which the prosthesis material may penetrate, whereby the gaiter is also securely anchored in the prothese. The gaiter prevents the penetration of contaminations through the slots 8 and at the same time ensures the resilient mobility of the lugs 9 in the prosthesis material.

FIG. 1 shows the position of the parts when the prosthesis is stressed. The spring 10 is compressed and the shoulder 15 abuts against the stop surface 14 of the front wall 16 of the sleeve 7. This limits the sinking-in of the prosthesis before the spring 10 is completely compressed. The pressure acting on the prosthesis is thus distributed in the required optimum manner on the one hand via the joint portion 1 on the anchor tooth 3 and on the other hand, over the gums located beneath the prosthesis. This, of course, prevents prosthesis on the side not connected with the anchor tooth from sinking any lower, which results in a slight swivelling of the joint portion 7 about the head 5 of the joint portion 1. This swivel movement may however, occur only in one plane. The stop surface 15 thus slides slightly towards the stop surface 14. If the prosthesis is unstressed, the spring 10 lifts the joint portion 7 together with the prosthesis to the stop of the head 5 against the lugs 9, whereby the desired relieving of the gums located below the prosthesis is obtained.

To remove the prosthesis, it is lifted until the lugs 9 of the sleeve 7 are deformed to such an extent that they slide-off, upwardly over the head 5. Conversely, to insert the prosthesis, the sleeve 7 is mounted on the head 5 whereby its lugs 9 snap-in over the head 5 and thus secure the prosthesis.

Various other embodiments are possible. It is possible, for example, for more lugs 9 to be provided than are shown. Other retention means may be provided on the sleeve 7.

What I claim is:

1. A joint for connecting a partial dental prosthesis with remaining natural teeth, having joint members connectable to an anchor tooth and with a part of the dental prosthesis and adapted to be telescoped in each other without clearance and capable of carrying out relative movements in one plane only, and a spring located between the two joint members and adapted to act therebetween in order with the unstressed partial dental prosthesis to relieve its support, the improvement wherein said joint comprises a stop on at least one of the joint members to limit the relative movement of the joint members in the direction of the spring force.

2. A joint according to claim 1, wherein said stop is constructed to limit the relative movement of the joint members so that the spring, adapted as a compression spring, cannot be completely compressed.

3. A joint according to claim 1, wherein one joint member has a neck to which is attached a spherical head which engages in the other sleeve-like joint member and wherein said stop comprises stop surfaces formed on the neck of the spherical head and on the wall of the other sleeve-like joint member facing the one joint member.

4. A joint according to claims 1, 2, or 3, wherein one joint member is a sleeve-like member provided at the open end of the sleeve with resiliently deformable, bent-in lugs for retaining the head of the other joint member, and wherein the lugs are surrounded by a soft plastics material sleeve or gaiter.

5. A joint according to claim 4, wherein the soft plastics material gaiter has perforations into which prosthesis material may penetrate to anchor the gaiter.

6. A joint according to claim 3, wherein said neck of said one joint member adjoins with an outer surface which is convexly rounded in correspondence with the head and merges tangentially into the surface of the head.

* * * * *